(12) United States Patent
Zhang et al.

(10) Patent No.: US 7,437,817 B2
(45) Date of Patent: Oct. 21, 2008

(54) PROCESS FOR FABRICATING HOLLOW ELECTROACTIVE DEVICES

(75) Inventors: Jindong Zhang, State College, PA (US); Robert E. Newnham, State College, PA (US)

(73) Assignee: The Penn State Research Foundation, University Park, PA (US)

(*) Notice: Subject to any disclaimer, the term of this patent is extended or adjusted under 35 U.S.C. 154(b) by 372 days.

(21) Appl. No.: 11/329,464

(22) Filed: Jan. 11, 2006

(65) Prior Publication Data

US 2006/0117552 A1    Jun. 8, 2006

Related U.S. Application Data

(62) Division of application No. 10/683,019, filed on Oct. 10, 2003, now Pat. No. 7,019,445, which is a division of application No. 09/836,441, filed on Apr. 17, 2001, now Pat. No. 6,654,993.

(60) Provisional application No. 60/221,859, filed on Jul. 28, 2000.

(51) Int. Cl.
    *H04R 31/00* (2006.01)

(52) U.S. Cl. .................. 29/594; 29/592.1; 29/602.1; 310/328; 310/371; 427/189; 427/190; 427/191; 427/192; 427/227

(58) Field of Classification Search ............... 29/592.1, 29/594, 602.1; 310/328, 371; 427/189–192, 427/227
See application file for complete search history.

(56) References Cited

U.S. PATENT DOCUMENTS

| 2,565,158 | A | | 8/1951 | William ................ 310/328 |
| 3,215,078 | A | | 11/1965 | Stec ................... 417/322 |
| 3,461,730 | A | | 8/1969 | Peters .................. 73/514.09 |
| 3,820,208 | A | | 6/1974 | Baldy .................. 29/25.35 |
| 4,224,525 | A | | 9/1980 | Phillips et al. ........... 250/531 |
| 4,829,812 | A | | 5/1989 | Parks et al. ............. 73/12.04 |
| 4,917,857 | A | | 4/1990 | Jaeckel et al. ............ 419/9 |
| 5,825,902 | A | * | 10/1998 | Fujishima .............. 381/190 |
| 5,861,702 | A | * | 1/1999 | Bishop et al. ........... 310/330 |
| 6,654,993 | B2 | * | 12/2003 | Zhang et al. ............ 29/25.35 |
| 6,820,313 | B2 | | 11/2004 | Gauchet ................ 29/25.35 |

* cited by examiner

*Primary Examiner*—Paul D Kim
(74) *Attorney, Agent, or Firm*—Ohlandt, Greeley, Ruggiero & Perle, L.L.P.

(57) ABSTRACT

A process for fabricating a ceramic electroactive transducer of a predetermined shape is disclosed. The process comprises the steps of providing a suitably shaped core having an outer surface, attaching a first conductor to the outer surface of the core, coating an inner conductive electrode on the outer surface of the core such that the inner conductive electrode is in electrical communication with the first conductor, coating a ceramic layer onto the inner electrode, thereafter sintering the ceramic layer, coating an outer electrode onto the sintered ceramic layer to produce an outer electrode that is not in electrical communication with the first conductor, and then poling the sintered ceramic layer across the inner electrode and the outer electrode to produce the ceramic electrode.

4 Claims, 4 Drawing Sheets

PROCESS FOR FABRICATING HOLLOW ELECTROACTIVE DEVICES

RELATED APPLICATION

This application is a division of U.S. patent application Ser. No. 10/683,019, filed Oct. 10, 2003 now U.S. Pat. No. 7,019,445, which is a division of U.S. patent application Ser. No. 09/836,441, filed Apr. 17, 2001 now U.S. Pat. No. 6,654,993, which claims priority from Provisional Patent Application Serial No. 60/221,859, filed Jul. 28, 2000.

FEDERALLY SPONSORED RESEARCH AND DEVELOPMENT

This invention was made with support from the Government under Contract No. N00014-96-1-1173. The Government has certain rights in the invention.

BACKGROUND OF THE INVENTION

1. Field of the Invention

The present invention relates to a process for fabricating highly uniform ceramic electroactive transducers. More particularly, the present invention relates to a process for fabricating hollow ceramic electroactive transducers, which are essentially spherical in shape.

2. Description of the Prior Art

A large number of medical procedures which require catheters are performed in the United States each year. Catheters are, typically, plastic tubes having a diameter of few millimeters. The uses of such catheters include, intravenous drug delivery, therapeutic device delivery, and other types of invasive procedures, such as, guiding balloon angioplasties of the leg, guiding catheters inside the heart to ablate incorrectly functioning cardiac tissue, and guiding catheters within the uterus to inject fluid into the fallopian tubes to test for tubal blockage.

Catheters must be guided to the proper location in the subject. One method of guiding catheters is to employ ultrasonic imaging. In doing so, an ultrasonic transducer is mounted on the catheter and a receiver is placed on the subject. When an ultrasound signal from the catheter mounted transducer strikes the external receiver, the signal is converted into an electronic marker corresponding to the precise location of the catheter in the ultrasound image of the subject.

At present, catheters are guided with real time X-ray imaging known as fluoroscopy. The use of ultrasound imaging has not found wide acceptance despite the advantages ultrasound has over X-ray technology.

A major encumbrance to using ultrasound imaging in guiding catheters is orientation-dependent ultrasound visibility of catheters known in the art. The orientation-dependent visibility, which plagues this technology, results from the wavelength of the ultrasound being several times smaller than the catheter is wide. The result is a catheter that becomes an ultrasound reflector, in addition to being an ultrasound transducer.

This produces an ultrasound visibility that is highly dependent on the orientation of the mounted transducer. X-ray fluoroscopy is not hindered by this phenomenon.

In one approach to eliminate orientation dependant ultrasonic visibility, an omnidirectional ultrasonic transducer is directly mounted on one end of the catheter. This approach solves the problem of signal orientation dependence on catheter orientation. To be suitable for this use, the ultrasonic transducer must be omnidirectional, possess low signal loss, have a high sensitivity, and preferably be uniform in construction and inexpensive to produce. Use of such an omnidirectional ultrasonic transducer mounted on a catheter would thus allow for replacement of the hazardous X-ray imaging commonly used in guiding catheters. The end result would be a more cost efficient, less dangerous procedure benefiting doctors, hospitals, and their patients.

Many different types of ultrasonic transducers such as thickness mode, polymer based, solid core and hollow core transducers are known in the art.

Thickness-mode ultrasonic transducers possess low signal loss, high sensitivity, and are inexpensive to produce. However, they are highly directional and as such, do not meet the omnidirectional requirement.

Polymer based piezoelectric materials can be easily fabricated into different shapes, including an omnidirectional geometry such as a sphere. However, polymer based piezoelectric materials possess high signal losses and low electromechanical coupling coefficients, which render polymer based transducers unsuitable for this use.

Solid core ceramic spherical transducers are omnidirectional. However, low sensitivity makes them less than suitable.

In contrast to the above transducers, hollow sphere ceramic electroactive transducers have the required omnidirectionality, low signal loss and high sensitivity required. In addition, they can be easily matched to electronic systems. Thus, hollow sphere ceramic electroactive transducers promise a natural solution to the problems associated with guiding catheters using ultrasound-imaging technology. However, given the current state of the art, it is extremely difficult to fabricate uniform hollow sphere ceramic electroactive transducers.

Presently, hollow sphere ceramic electroactive transducers can be produced by machining and grinding bulk ceramic into hemispheres. An electrode is then formed on the inner surface of the hemispheres, followed by bonding of two such hemispheres together. This approach is labor intensive, high cost, and low in productivity.

U.S. Pat. No. 4,917,857 to Jaeckel et al. is directed to a process for the production of metallic or ceramic hollow spheres to make a reticulate structure. In this process, foamed polymer cores are coated with a suspension containing metal or ceramic particles in a bed reactor. The polymer core is later pyrolyzed to obtain a metal or ceramic hollow sphere. A hollow sphere ceramic electroactive transducer can be prepared using hollow ceramic spheres obtained from this process by first opening a small hole in the sintered sphere, normally by polishing. Next, an inner electrode is deposited on the inner surface of the hollow sphere through the hole. An outer electrode is then deposited on the outer surface of the sphere. The ceramic is then poled under an electric field. However, this method, and the transducers produced by this method have low green density. In addition, the ceramic shells contain many pores due to the forming process that hinder subsequent sintering of the green ceramic body. The pores become defects in the surface of the sintered sphere, leading to mechanical fractures and decreased sensitivity when the spheres are processed into hollow sphere ceramic electroactive transducers.

Additionally, the hole created is mechanically weak. This weakness limits the hydrostatic pressure tolerance of the transducers produced in this fashion. When used in underwater applications, the depth capability of these transducers is drastically reduced.

Thus, as discussed above, the crude fabrication techniques present in the art do not allow for hollow ceramic electroactive transducers to be produced uniformly, in commercially significant quantities, at a cost low enough to make this technology appealing.

SUMMARY OF THE INVENTION

The present invention includes a process for fabricating a ceramic electroactive transducer of a predetermined shape. The process includes the steps of: (a) providing a suitably shaped core having an outer surface; (b) attaching a first conductor to the outer surface of the core; (c) coating an inner conductive electrode on the outer surface of the core such that the inner conductive electrode is in electrical communication with the first conductor; (d) coating a ceramic layer onto the inner electrode; thereafter (e) sintering the ceramic layer; (f) coating an outer electrode onto the sintered ceramic layer to produce an outer electrode that is not in electrical communication with the first conductor; and (g) poling the sintered ceramic layer across the inner electrode and the outer electrode to produce a ceramic electroactive transducer.

The present invention further includes a process for fabricating a ceramic electroactive transducer of a predetermined shape which is multi-layered. The process includes the steps of: (a) providing a suitably shaped core having an outer surface; (b) attaching a first conductor to the outer surface of the core; (c) coating a first inner conductive electrode on the outer surface of the core such that the first inner conductive electrode is in electrical communication with the first conductor; (d) coating a first ceramic layer having an outer surface on the first inner electrode; thereafter (e) attaching a second conductor to the outer surface of the first ceramic layer; (f) coating a second inner conductive electrode on the outer surface of the first ceramic layer such that the second inner conductive electrode is in electrical communication with the second conductor without being in electrical communication with the first conductor; (g) coating a second ceramic layer having an outer surface on the second inner electrode; thereafter (h) sintering the first and the second ceramic layers; (i) coating an outer electrode on the second sintered ceramic layer to produce an outer electrode that is not in electrical communication with the first conductor or with the second conductor; and (j) poling the first and the second sintered ceramic layers across the first inner electrode, the second inner electrode, and the outer electrode.

The present invention still further includes a process for fabricating a plurality of ceramic electroactive transducers, which have a predetermined spatial relationship of a predetermined shape. This process includes the steps of: (a) providing a plurality of suitably shaped cores, each having an outer surface, arranged in the predetermined spatial relationship; (b) attaching one or more first conductors to the cores; (c) coating an inner conductive electrode on each of the outer surfaces of the cores such that the inner conductive electrodes are in electrical communication with at least one of the first conductors; (d) coating a ceramic layer on each of the inner electrodes; thereafter (e) sintering the ceramic layers; (f) coating one or more outer electrodes on each of the sintered ceramic layers to produce a plurality of outer electrodes not in electrical communication with the first conductor; and (g) poling the sintered ceramic layers across the inner electrodes and the plurality of the outer electrodes.

The present invention provides for hollow ceramic electroactive transducers by using a core formed from a thermally decomposable material, and further including the step of heating the layered ceramic under conditions sufficient to remove the core prior to the sintering step.

In addition, the process further provides for encapsulating the ceramic electroactive transducer in a non-conductive material after coating with the outer electrode.

The present invention provides a simple, low cost process to produce ceramic electroactive transducers that have a uniform inner electrode. The present invention also can produce large quantities of, for example, spherical ceramic electroactive transducers having a diameter ranging from about several tenths of a millimeter to several meters. In addition, the present invention eliminates the need for machining and polishing, is simple and economical, and substantially improves the uniformity and reproducibility of the end product.

BREIF DESCRIPTION OF THE DRAWINGS

DETAIL DESCRIPTION OF THE INVENTION

Figure 1A:
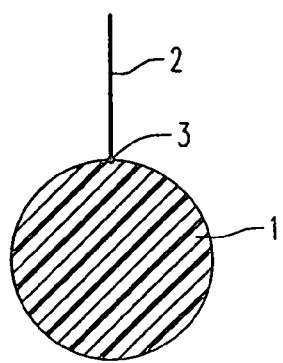
FIG. 1a is a cross sectional view illustrating the core with the first conductor attached via a binder.
Figure 1B:
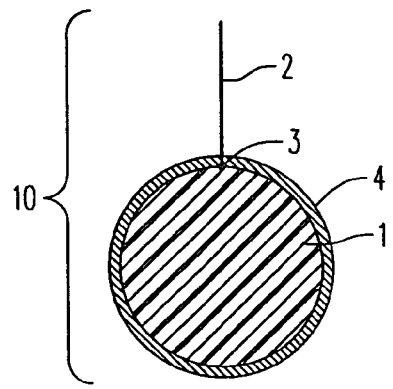
FIG. 1b is a cross sectional view illustrating the first conductor-attached core coated with the inner electrode.

Referring to the figures and particularly to FIG. 1, core 1 is preferably a thermally decomposable polymer, most preferably core 1 is made of polystyrene. To achieve a ceramic layer with high green density, core 1, or hollow core 1 with a porous outer surface is preferred.

First conductor 2, is a metal, a metal alloy, a conducting ceramic, a semi-conductor, or a combination thereof. The first conductor is preferably a thin metal or metal alloy wire, most preferably a Pt or Ni wire, having a diameter of less than about 5 mm, preferably less than about 1 mm. This first conductor 2 is used to apply voltage to the inner electrode 4.

The first conductor is attached to the core 1 and secured in position using a suitable binder 3. The binder 3, is preferably a thermally decomposable binder (e.g. PVA).

The inner electrode 4 is then coated onto the outer surface of the core 1. The inner electrode is either an electrical conductor or a semi-conductor, preferably a metal, and most preferably Pt, Ni, or a combination thereof. The core 1 is coated with the inner electrode, preferably by contacting the core 1 with a slurry containing a dispersed powder of the electrode material in a solvent (i.e., a metal ink). The powder is preferably a metal powder having an average particle size of about 10 microns or smaller. The inner electrode slurry can also contain at least one suitable co-solvent, binder, dispersant, antifoam, or a combination thereof.

Excess inner electrode material from the coating step can be removed to provide a uniform thickness of the inner electrode 4. The inner electrode then serves as a substrate onto which the green un-sintered ceramic layer 5 is deposited or coated.

The green ceramic layer or shell 5 is coated or deposited directly on top of the inner electrode 4, preferably by contacting or dipping the substrate into a well-dispersed ceramic slurry.

The ceramic slurry contains a solvent, and a plurality of suitable ceramic particles. Optionally, the slurry contains at least one suitable co-solvent, binder, dispersant, antifoam, or a combination thereof.

Suitable ceramic particles can include, but are not limited to, PZT, PMN, metal titanates including: barium titanate, bismuth titanate, bismuth iron titanate, and a combination thereof. The ceramic particles have an average size less than about 50 microns, preferably less than about 10 microns.

The ceramic layer 5 has a thickness greater than about 0.001 mm. The layer thickness can be modified by the time the core is placed in contact with the slurry in a particular contacting step, also by the number of contacting steps conducted. The coating process typically involves a single immersion of the core in the slurry for approximately one second.

The loading of ceramic particles in the slurry can also control the ceramic layer thickness. The solids loading in the ceramic slurry is from about 1% to about 90% by volume, preferably from about 20% to about 55% by volume.

Suitable solvents and co-solvents in the slurry include, water, and organic solvents including, but not limited to alcohols, ketones, esters, hydrocarbons, aromatic hydrocarbons, amines, hetero-aromatic hydrocarbons, and mixtures thereof.

Suitable binders can include, but are not limited to, wax, polyethylene glycol, paraffin, polyvinyl alcohol, methyl cellulose, starch, and a combination thereof. The total amount of binder in the slurry is less than about 10% by volume, preferably less than about 1%.

Suitable dispersants that stabilize the slurry, adjust pH, and prevent formation of agglomeration can include, but are not limited to, cationic surfactants, non-ionic surfactants, anionic surfactants, carbonic acid and salts, silicic acid and salts, polyacrylate and salts, citric acid and salts, polymethacrylate and salts, and a combination thereof. Dispersants are less than about 10% of the total slurry by volume, preferably less than about 2%.

Suitable antifoams or defoaming agents can include, but are not limited to, fluorocarbons, dimethylsilicones, higher molecular weight alcohols, glycols, salts of stearic acid, and a combination thereof. Antifoam is less than about 5% by volume of the total slurry, preferably less than about 0.5%.

The viscosity of the ceramic slurry is less than about 5000 mPa·s, preferably less than about 2000 mPa·s.

After coating the inner electrode containing core 10 with the ceramic slurry, excess slurry can be removed by mechanical means, such as spinning, to insure formation of a uniform green ceramic layer.

It is important to note that a porous polystyrene core and the inner electrode both absorb water from the wet ceramic layer. Capillary action produces a dense green ceramic layer, which is crucial to fabricating a fully densified ceramic body.

Figure 1C:
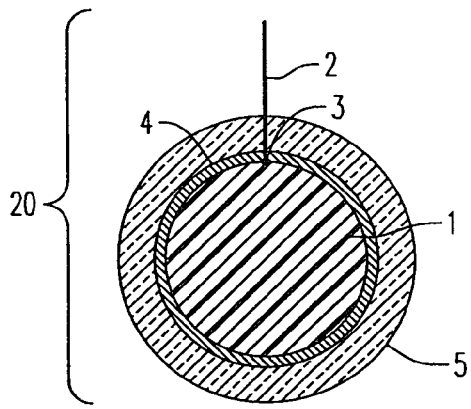
FIG. 1c is a cross sectional view illustrating the first conductor-attached core, coated with the ceramic layer on top of the inner electrode.
Figure 1D:
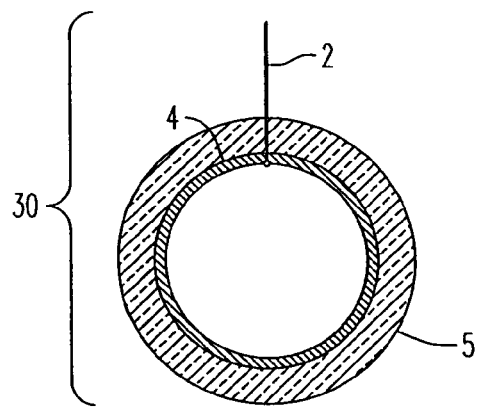
FIG. 1d is a cross sectional view illustrating the sintered ceramic layer with the inner electrode attached to the first conductor, with the inner core having been thermally removed.

After coating the core 1 with the inner electrode 4 and the ceramic layer 5 to produce unit 20 as shown in FIG. 1c, the layers can be dried via the application of heat. Preferably, the unit 20 is subjected to the thermal core removal step, commonly referred to as core burnout, wherein the core is thermally removed from within the layers by subjecting the unit 20 to temperatures from about 100° C. to about 900° C., preferably from about 300° C. to about 700° C., for a period of time sufficient to thermally remove the core 1, solvents, co-solvents, binders, antifoams, and dispersants from within the unit 20 to produce a hollow unit 30 as shown in FIG. 1d. This step can be carried out in a metal vapor rich atmosphere to prevent metals contained in the ceramic layer 5 from being leached out. Optionally, the thermal removal step can be carried out in an essentially oxygen free environment to prevent oxidation of first conductor 2 and inner electrode 4. The step is carried out under such conditions that the inner electrode 4 and the ceramic layer or shell 5 remain in contact and physically intact.

The temperature of the thermal core removal (burnout) step is preferably increased from ambient to a desired final temperature at rates from about 0.1° C./min to about 20° C./min, preferably at about 1° C./min. The unit is maintained at the final temperature until such time as the core 1, solvents, co-solvents, binders, antifoams, and dispersants are sufficiently removed. The final temperature hold time is typically about several hours.

At this stage in the process, a hollow unit 30 is produced which includes a hollow green ceramic shell 5 with a protruding first conductor 2 attached to an inner electrode 4 as shown in FIG. 1d.

Next, hollow unit 30 is sintered under conditions that vary according to the ceramic composition. Typically, the ceramic and electrode materials are sintered in the temperature range from about 900° C. to about 2000° C., preferably from about 1200° C. to about 1400° C. The sintering temperature and time need to be adjusted experimentally to achieve the desired density of the particular ceramic material and layer thickness used. For metal containing ceramic compositions, i.e., lead, bismuth, barium, the ceramic layer can be sintered in a metal rich atmosphere to reduce the metal loss from the ceramic body. Optionally, hollow unit 30 can be sintered in an essentially oxygen free atmosphere to prevent oxidation of the first conductor and the inner electrode. The upper temperature limit of the sintering step should not exceed the melting point of the inner electrode, else a uniform inner electrode in contact with the ceramic layer cannot be obtained.

Figure 2:
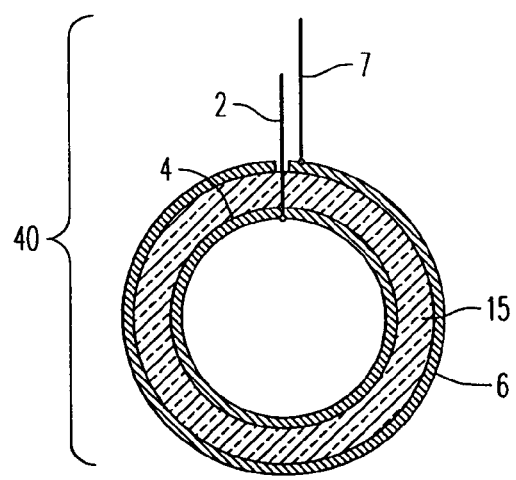
FIG. 2 is a cross sectional view illustrating a hollow sphere ceramic electroactive transducer coated with an outer electrode.

After sintering and cooling, the outer surface of the sintered ceramic shell 15 (see FIG. 2) is coated with an outer electrode 6. The outer electrode is preferably metal and most preferably silver metal. Coating can be accomplished by contacting the sintered surface with the metal, or a metal ink through sputtering or dipping. A second conductor 7, preferably a thin lead wire can then be electrically attached to outer electrode 6.

The sintered ceramic shell 15 is then poled with an electric field having a strength from about 500 V/mm to about 5000 V/mm, preferably from about 1000 V/mm to about 3000 V/mm. The poling can be carried out at elevated temperatures in the range from about 50° C. to about 300° C. This completes the process of fabricating a hollow ceramic electroactive transducer 40.

The cores recited in the present invention can be of any suitable geometric shape, for example, spherical cores for hollow spheres, cylinder cores for tubes, cubic cores for hollow cubes etc.

In a further embodiment of the present invention, the ceramic cores mentioned above can be machined or ground to produce derivative shapes at any point during the process. These derivative shapes being defined by the original shape of the core as intersected by at least one plane partially, or completely therethrough. For the purpose of example only, a hollow cylinder shaped green ceramic or sintered ceramic can have the ends removed, either prior to or after poling in the case of the sintered ceramic, to produce a hollow tube shaped ceramic electroactive transducer. A spherical device can also be ground or machined to produce a hemi-spherical or shell-shaped ceramic electroactive transducer.

Figure 5:
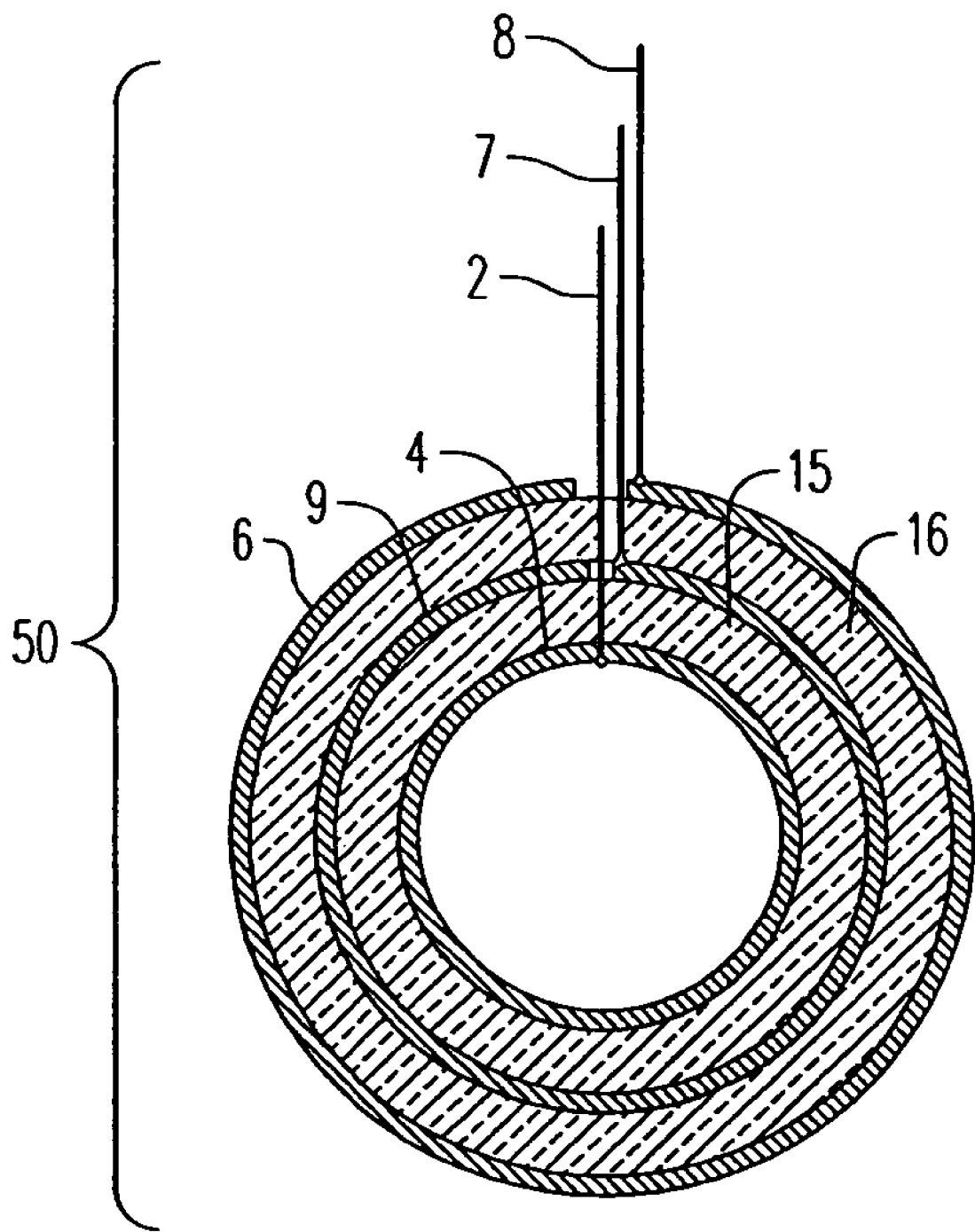
FIG. 5 is a cross sectional view illustrating the fabrication of a hollow sphere ceramic electroactive transducer with multiple conductors, ceramic layers and electrodes.

The present invention can also produced a multilayered hollow ceramic electroactive transducer as shown in FIG. 5. In addition to a first conductor 2, an inner electrode 4, and a ceramic layer 15, additional conductors 7, and alternating layers of electrodes 9, and ceramic layers 16 are fabricated by repeating the steps of attaching a conductor 7 to green ceramic layer 5 with subsequent coating of ceramic layer 5 with additional electrode 9, followed by coating additional electrode 9 with additional ceramic layer prior to the core removal step with subsequent sintering as described above. Upon sintering, the most outer ceramic layer 16 is coated with outer electrode 6, and the sintered ceramic layers 15 and 16 are poled as described above to produced the multi-layered ceramic electroactive transducer 50.

Figure 6A:
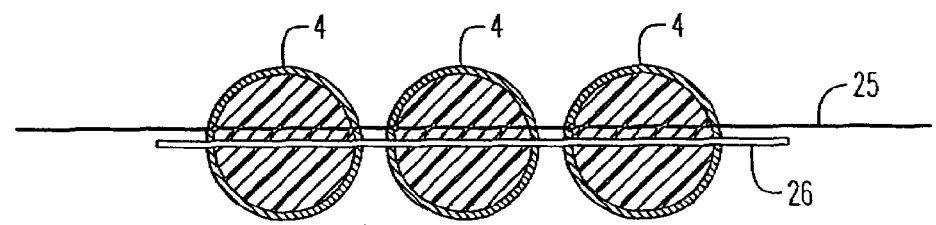
FIG. 6a is a cross sectional view illustrating a plurality of cores in spatial relationship attached to a first conductor.
Figure 6B:
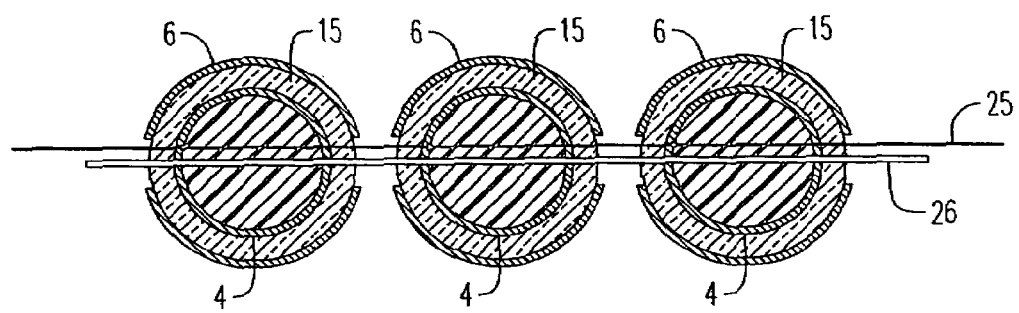
FIG. 6b is a cross sectional view illustrating a plurality of hollow ceramic electroactive transducers in spatial relationship.
Figure 7:
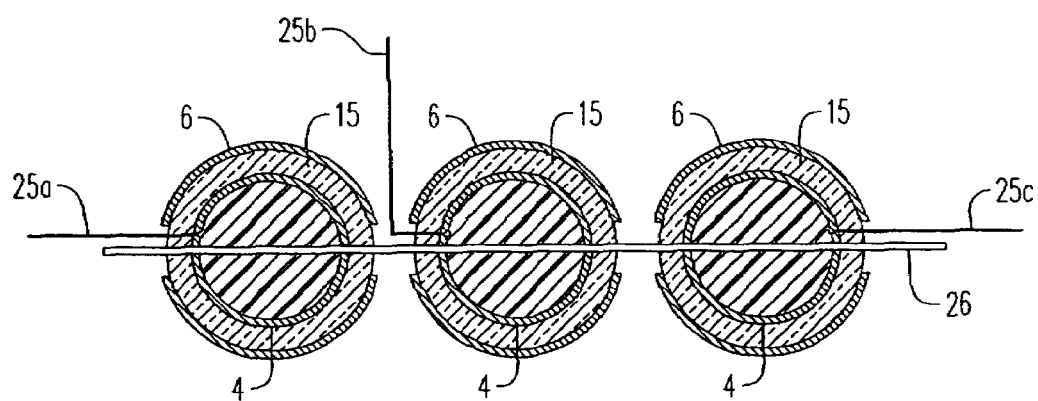
FIG. 7 is a cross sectional view illustrating a plurality of hollow ceramic electroactive transducers in spatial relationship with isolated inner electrodes.

Referring to FIG. 6a, a plurality of cores can be attached to at least one conductor 25 or other support 26 to fabricate a predetermined spatial relationship, i.e., two-dimensional or three-dimensional array, of ceramic electroactive transducers. As shown in FIG. 6b, the inner electrodes can be in electrical communication with one conductor, optionally the inner electrodes can be electrically isolated with one-another through the use of a plurality of conductors 25a, 25b and 25c as shown in FIG. 7.

The size limit of the present invention is controlled by the size of the core, and the ability to coat the cores in a uniform manner. Hollow ceramic electroactive transducers having diameters of several tenths of a millimeter are easily fabricated using the steps of the present invention.

The present invention is further described in the following examples, which are intended to be illustrative and not limiting.

EXAMPLE 1

Deionized water was added to PZT powder containing PVA binders (available from Vernitron Piezoelectric Division) to form a ceramic slurry with a solids loading of 20 vol %. The slurry was ball milled to break up agglomerates and aggregates followed by sieving and evacuation to remove entrapped air. A porous polystyrene sphere of 2.5 mm in diameter was secured to the end of a 0.4 mm diameter platinum wire using PVA as the binder. The inner electrode was coated onto the core by dipping the core into commercially available platinum ink (available from Ferro Electronic Materials Division, El 192 Pt Internal Electrode) that had been diluted with acetone. The inner electrode coated sphere was then dried at room temperature prior to being dipped into the above ceramic slurry. The excess slurry was removed by spinning the dipped core at the end of the Pt wire.

After being dried at room temperature, the core was thermally removed by placing the unit in an oven and increasing the temperature from ambient to 350° C. at 1° C./min. The unit was held at 350° C. for one hour, and then the temperature was increased to 550° C. at 1° C./min. The unit was then held at 550° C. for an additional two hours. A hollow green-ceramic layer with an inner electrode was obtained. The hollow unit was then sintered at 1285° C. for 1.5 hours in a closed alumina crucible with a PZT powder bed.

After cooling the sintered unit, the platinum wire was coated with an insulating epoxy prior to coating the outer layer on with an air-dry silver ink. A thin silver lead wire was attached to the outer electrode with silver conductive epoxy.

The sintered ceramic layer was then poled under an electric-field strength of 2000 V/mm, while being heated to 150° C. in a silicon oil bath. The hollow ceramic electroactive transducer was then encapsulated in a non-conductive resin and evaluated.

Figure 3:
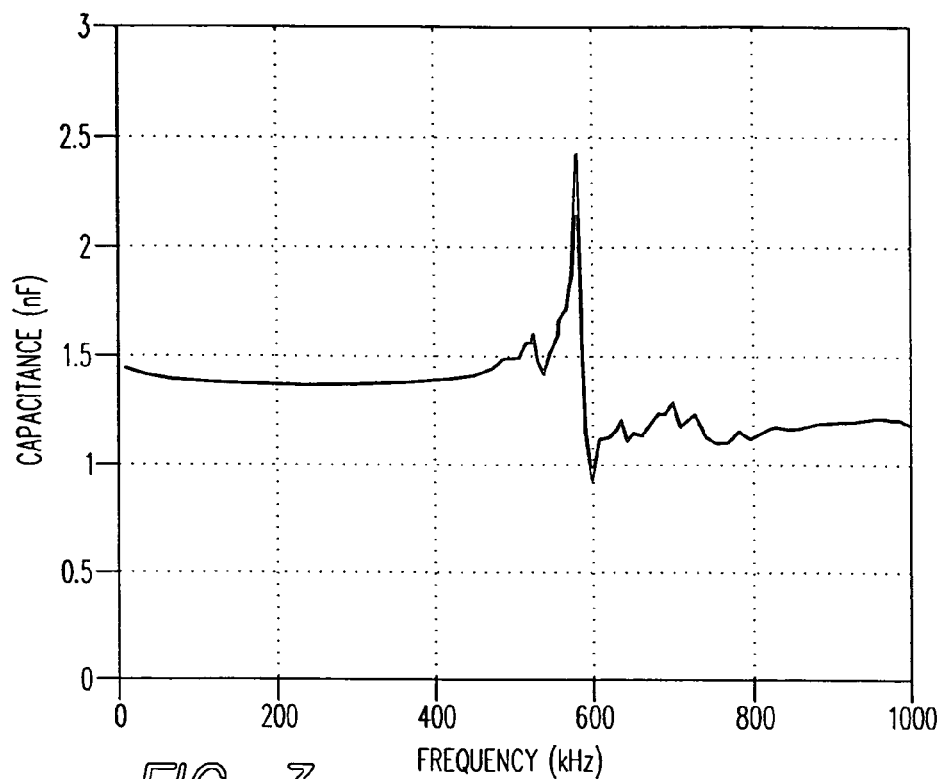
FIG. 3 is a graphical representation of the measured capacitance of a radially poled hollow sphere ceramic electroactive transducer fabricated according to the present invention.
Figure 4:
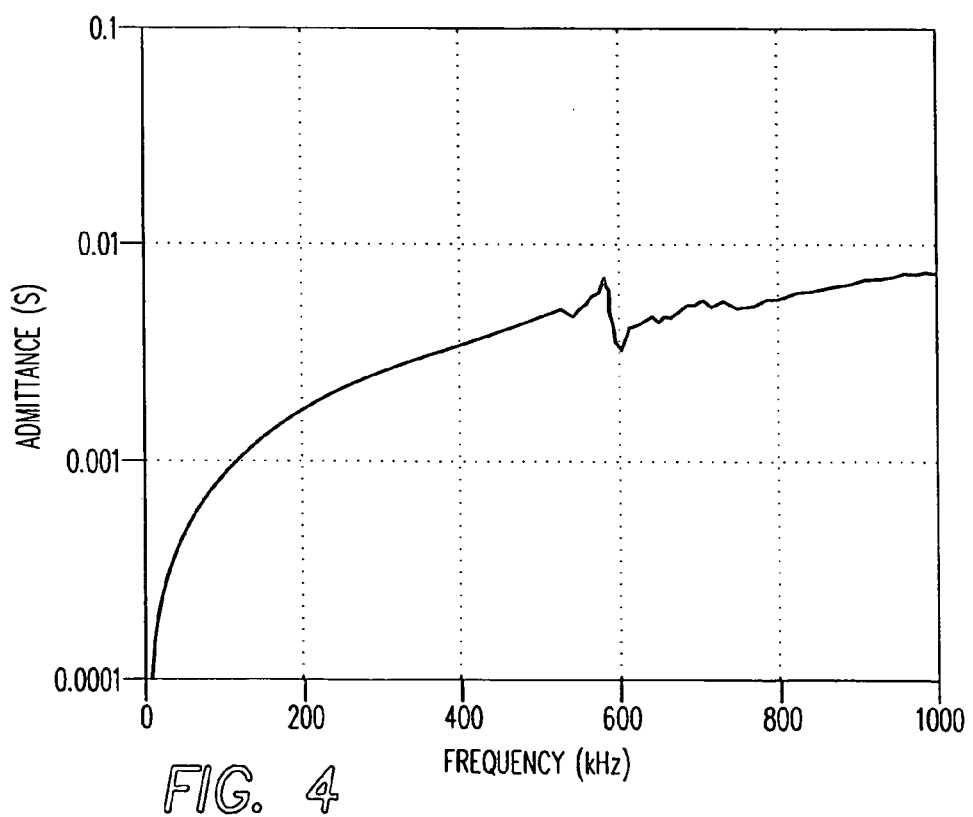
FIG. 4 is a graphical representation of the measured admittance of the hollow sphere ceramic electroactive transducer of FIG. 3.

As shown in FIG. 3, the hollow sphere ceramic electroactive transducer of Example 1 had a measured capacitance of 1.4 nF, which is in agreement with the calculated value. FIG. 4 shows the measured admittance of this hollow sphere ceramic electroactive transducer.

EXAMPLE 2

A spherical multilayer ceramic electroactive transducer as shown in FIG. 5, was fabricated by following the process of Example 1, with the exception of attaching an additional conductor to the first ceramic layer which was then coated with an additional electrode, followed by coating with an additional layer of ceramic as described in Example 1 above. Care was taken to insure the second electrode layer did not touch the platinum wire used for the first conductor.

The core was then thermally removed and the hollow unit sintered as in Example 1 above. An outer electrode was coated on the outer ceramic layer, and the sintered ceramic layers poled as outlined above.

It was unexpectedly discovered that connecting the inner electrode in parallel to the additional electrode enhanced the pressure output of the transducer, and connecting the two electrodes in series enhanced the receiver sensitivity of the transducer.

EXAMPLE 3

A linear array of hollow spherical ceramic electroactive transducers was fabricated by first providing an array of 2.5 mm polystyrene spherical cores threaded on a Pt wire having a 0.4 mm diameter. As described in Example 1, the cores were coated with an inner electrode and then coating with a ceramic layer prior to thermally removing the core and sintering the array of connected hollow units. The sintered ceramic layers of the array were then coated with an outer electrode and poled to produce an array of hollow ceramic electroactive transducers. The array was then encapsulated in a non-conductive resin to maintain the desired spatial arrangement.

The present invention has been described with particular reference to the preferred embodiments. It should be understood that variations and modifications thereof can be devised by those skilled in the art without departing from the spirit and scope of the present invention. Accordingly, the present invention embraces all such alternatives, modifications and variations that fall within the scope of the appended claims.

What is claimed is:

1. A process for fabricating a ceramic electroactive transducer of a predetermined shape comprising the steps of:

(a) providing a suitably shaped core having an outer surface;
(b) attaching a first conductor to said outer surface of said core;
(c) coating a first inner conductive electrode on said outer surface of said core such that said first inner conductive electrode is in electrical communication with said first conductor;
(d) coating a first ceramic layer having an outer surface on said first inner electrode; thereafter
(e) attaching a second conductor to said outer surface of said first ceramic layer;
(f) coating a second inner conductive electrode on said outer surface of said first ceramic layer such that said second inner conductive electrode is in electrical communication with said second conductor without being in electrical communication with said first conductor;
(g) coating a second ceramic layer having an outer surface on said second inner electrode; thereafter
(h) sintering said first and said second ceramic layers;
(i) coating an outer electrode on said second sintered ceramic layer to produce an outer electrode that is not in electrical communication with said first conductor or with said second conductor;
(j) poling said first and said second sintered ceramic layers across said first inner electrode, said second inner electrode, and said outer electrode; and
(k) adding a plurality of additional conductors, electrodes, and ceramic layers prior to said sintering step.

2. The process of claim 1 wherein said plurality of additional electrodes are electrically isolated from each other, from said inner electrode, and from said outer electrode.

3. A process for fabricating a plurality of ceramic electroactive transducers having a predetermined spatial relationship of a predetermined shape comprising the steps of:
(a) providing a plurality of suitably shaped cores, each having an outer surface, arranged in said predetermined spatial relationship;
(b) attaching one or more first conductors to said cores;
(c) coating an inner conductive electrode on each of said outer surfaces of said cores such that said inner conductive electrodes are in electrical communication with at least one of said first conductors;
(d) coating a ceramic layer on each of said inner electrodes; thereafter
(e) sintering said ceramic layers;
(f) coating one or more outer electrodes on each of said sintered ceramic layers to produce a plurality of outer electrodes not in electrical communication with said first conductor; and
(g) poling said sintered ceramic layers across said inner electrodes and said plurality of said outer electrodes.

4. The process of claim 3, wherein said predetermined spatial relationship is changeable at any step of said fabricating process.

* * * * *